United States Patent
Hermens et al.

(10) Patent No.: US 9,840,694 B2
(45) Date of Patent: Dec. 12, 2017

(54) REMOVAL OF CONTAMINATING VIRUSES FROM AAV PREPARATIONS

(75) Inventors: Wilhelmus Theodorus Johannes Maria Christiaan Hermens, Amsterdam (NL); James Patrick Smith, Amsterdam (NL)

(73) Assignee: uniQure IP B.V., Amsterdam (NL)

( * ) Notice: Subject to any disclaimer, the term of this patent is extended or adjusted under 35 U.S.C. 154(b) by 58 days.

(21) Appl. No.: 14/343,884

(22) PCT Filed: Sep. 7, 2012

(86) PCT No.: PCT/NL2012/050619
§ 371 (c)(1),
(2), (4) Date: Jul. 8, 2014

(87) PCT Pub. No.: WO2013/036118
PCT Pub. Date: Mar. 14, 2013

(65) Prior Publication Data
US 2014/0342434 A1    Nov. 20, 2014

Related U.S. Application Data

(60) Provisional application No. 61/532,176, filed on Sep. 8, 2011.

(30) Foreign Application Priority Data

Sep. 8, 2011    (EP) .................................. 11180594

(51) Int. Cl.
*C12N 7/00*    (2006.01)
*B01D 61/14*    (2006.01)
(Continued)

(52) U.S. Cl.
CPC ............. *C12N 7/00* (2013.01); *B01D 61/145* (2013.01); *B01D 61/16* (2013.01); *B01D 71/10* (2013.01); *C12N 7/02* (2013.01); *B01D 2311/04* (2013.01); *B01D 2311/26* (2013.01); *B01D 2311/2623* (2013.01); *B01D 2311/2649* (2013.01); *C12N 2710/14051* (2013.01);
(Continued)

(58) Field of Classification Search
None
See application file for complete search history.

(56) References Cited

U.S. PATENT DOCUMENTS 6,479,273 B1    11/2002 Bogedain et al.

FOREIGN PATENT DOCUMENTS

JP    2001-513644 A    9/2001
WO    2010148143 A1    12/2010

OTHER PUBLICATIONS

Negrete and Kotin. Strategies for manufacturing recombinant adeno-associated virus vectors for gene therapy applications exploiting baculovirus technology. Brief Funct Genomic Proteomic. Jul. 2008;7(4):303-11.*

(Continued)

*Primary Examiner* — Michelle S Horning
(74) *Attorney, Agent, or Firm* — Gilberto M. Villacorta; Sunit Talapatra; Foley & Lardner LLP

(57) ABSTRACT

The present invention relates to a separation of viruses of an essentially spherical shape from viruses with a rod-like shape that are comprised in a sample, wherein the sample comprising the viruses is subjected to filtration.

19 Claims, 2 Drawing Sheets

(51) Int. Cl.
*B01D 61/16* (2006.01)
*B01D 71/10* (2006.01)
*C12N 7/02* (2006.01)

(52) U.S. Cl.
CPC .............. *C12N 2750/14051* (2013.01); *C12N 2750/14332* (2013.01); *C12N 2750/14351* (2013.01)

(56) References Cited

OTHER PUBLICATIONS

Smith et al. A simplified baculovirus-AAV expression vector system coupled with one-step affinity purification yields high-titer rAAV stocks from insect cells. Mol Ther. Nov. 2009;17(11):1888-96.*
Michalsky et al. Concentration of the baculovirus Autographa californica M nucleopolyhedrovirus (AcMNPV) by ultrafiltration. Desalination 250 (3) (2010) p. 1125-1127.*
Rohrmann, GF et al., "Introduction to the baculoviruses and their taxonomy." Baculovirus Molecular Biology, p. 1-12 (Nov. 2008).
Thorne, Barbara A., et al. "Characterizing clearance of helper adenovirus by a clinical rAAV1 manufacturing process." Biologicals, 36:7-18 (2008).
Blumel J et al., "Wichtige Aspekte der Virussicherheit bei Neuartigen Therapien" Bundesgesundheitsblatt—Gesundheitsforschung-Gesundheitsschutz 53:38-44 (2009).
Blumel J. "Virus Safety Aspects of Advanced Therapies", DGRA-Symposium, "Advanced Therapy Medicinal Product Development and Regenerative Medicine" pp. 1-18, (Nov. 2008).
Rueda P. et al., "Effect of different baculovirus inactivation procedures on the integrity and immunogenicity of porcine parvovirus-like particles", Vaccine 19:726-734 (2000).
Kern G., "Virus removal by filtration", Biopharm International, 19-10:32-41 (2006).
International Search Report, Application No. PCT/NL2012/050619, (Oct. 9, 2012).
Wikipedia entry for "Affinity Chromatography", pp. 1-4 (Dec. 18, 2015).
Third Office Action in corresponding Chinese Patent Application 201280049899.5, dated Apr. 13, 2016. (English Translation).
Classification of Viruses, Chapter 8 Insect DNA Viruses, Higher Education Press, pp. 1-5 (Apr. 5, 2016) (English translation).
Burnouf et al., "Nanofiltration of plasma-derived biopharmaceutical products", Haemophilia, 2003, vol. 9, pp. 24-37.

* cited by examiner

REMOVAL OF CONTAMINATING VIRUSES FROM AAV PREPARATIONS

FIELD OF THE INVENTION

The present invention relates to the fields of virology and gene therapy. In particular, the invention relates to a method for removing contaminating viruses with a rod-like shape, such as e.g. baculovirus, from preparations of virus with an essentially spherical shape, such as e.g. adeno-associated viral gene therapy vectors.

BACKGROUND OF THE INVENTION

In the production of viral vectors for use in gene therapy replication-deficient viruses are used for reasons of safety. Replication-deficient viruses are able to infect a human cell in vivo and transfer the transgene into the cell, but are unable to replicate in the cell by themselves. Typically, this is achieved by deleting viral genes which are important for virus replication, such as for example rep and cap genes. This also allows for incorporation of gene product(s) of interest in place of the viral genes. For the generation of virus particles in a host cell, the viral genes that are deleted from the replication-deficient virus need to be provided separately, for instance by providing helper viruses.

Adeno-associated virus (AAV) is a non-autonomously replicating virus that belongs to the Parvoviridae family and constitutes a single-stranded molecule of DNA with an outer icosahedral coat of structural protein having a diameter of approx. 18 to 26 nm. Wild type AAV viruses can either integrate into the genome of the host cell or replicate in the host cells in the presence of a helper virus. Adenoviruses were first identified as possible helper viruses. However, other essentially spherically shaped mammalian helper viruses, such as the herpes viruses, which are pathogenic to humans and animals, are also suitable. In recent years, adeno-associated virus (AAV) vector production by means of baculovirus-based expression systems in insect cells (Urabe et al. [2002] Hum Gene Ther. 13(16):1935-43) has become increasingly popular since the system is easily scalable for industrial applications of gene therapy. In this production system typically three recombinant baculoviruses are used encoding the AAV rep genes, the AAV cap genes and the gene product of interest (transgene DNA) flanked by AAV inverted terminal repeats (ITRs).

A significant disadvantage associated with the preparation of viral vectors using helper viruses or virus-based expression systems is the formation of a mixed population of product virus particles and helper viruses, which has to be subjected to further purification. Contaminating viruses, such as for example adenovirus or baculovirus, have to be avoided or minimized when using viral vectors in gene therapy because of the potential pathogenicity and/or immunogenicity of the contaminating virus.

Several methods for elimination of helper viruses are presently known in the art, however, they all have their disadvantages. Examples of these methods are density gradient centrifugation or heat inactivation or a combination thereof. However, density gradient centrifugation is only economically feasible on relatively small volumes and thus this method is not feasible on an industrial scale. Heat inactivation is based on the different thermal stabilities of AAV and the helper viruses. For example, heating a mixed population of adenovirus and AAV to 56-65° C. leads to more or less selective heat inactivation of the helper virus with only a slight loss in the activity of the AAV. Unfortunately, the denatured helper virus proteins which would be still present in the sample and upon use in gene therapy be able to evoke a cellular immune response in the patient (Smith, C. A. et al. (1996) J. Virol., 70, 6733-6740).

In addition, column chromatographic methods, including ion exchange (anion and/or cation based) and affinity chromatography, have been developed to purify AAV vectors. Those methods result in highly enriched preparations of AAV vector, but they cannot be validated alone to show sufficient depletion of helper viruses to meet the regulatory requirements of marketed pharmaceutical products.

Finally, in U.S. Pat. No. 6,479,273 it is disclosed that separation of recombinant AAV and adenovirus, i.e., two essentially spherical viruses of substantially different diameter is achieved by subjecting a solution containing both viruses to one or more filtrations through a filter membrane with a pore size of approximately 50 nm or a filter membrane with a pore size of approximately 35 nm rAAV is disclosed to have a diameter of approx. 25 nm and adenovirus is said to have a diameter of approx. 65-90 nm, although larger diameters, e.g. close to 100 nm, have been reported in literature [Kennedy and Parks (2009) Molecular Therapy 17(10):1664-1666; Berkowitz (2003) WCBP $7^{th}$ annual meeting Jan. 7-10, 2003, San Francisco, Calif.]. However, contaminating viruses that result from AAV vector production by means of a baculovirus-based expression system in insect cells, are derived from the baculoviridae and thus are rod-shaped, with a length of approximately 260 nm and a diameter of approximately 20 nm. Since (recombinant) AAV is substantially spherical and has a diameter of approximately 18 to 26 nm, the baculovirus partially has (in two dimensions) a similar size to the target virus.

Regulatory requirements, for example the viral safety evaluation of biotechnology products derived from cell lines of human or animal origin (ICH Q5A (R1)) by the European Medicines Agency (EMA), require that the process for the purification of a biological pharmaceutical is capable of removing any non-product virus. The removal of viral contaminants is performed by "viral clearance" or "viral removal" process steps and is usually obtained by chromatography and/or virus filtration. Also "virus inactivation" process steps are used to attenuate potential pathogenic effects caused by non-product viruses. This usually contains extreme physical conditions (e.g. pH, Temperature) and/or chemical conditions (e.g., detergents, solvents). Pharmaceutical products are usually proteins of less than approximately 200 kDa and "virus removal" processes are well established. However, a relatively new type of products concern gene therapy products that comprise viruses of a few thousand kDa for which "virus removal" processes are not well documented. In particular, a process of "virus removal" in which the pharmaceutical product is a spherical virus and the viral contaminant is a rod-shaped virus is not documented yet.

Therefore, there is a need in the art for additional separation/purification methods that are technically and economically feasible to be employed on industrial scale and that are capable of partly or completely removing a non-product virus of a virus-based expression system, from a sample containing AAV, preferably a recombinant AAV sample obtained from a baculovirus-based expression system. Thereby reducing the potential pathogenicity and/or immunogenicity of the non-product virus. In particular there is a need in the art for additional separation/purification methods where the non-product virus is rod-like shaped that has a length of several times the diameter of AAV, but has a similar diameter as the AAV.

DESCRIPTION OF THE INVENTION

Brief Description of the Invention

In a first aspect, the present invention relates to a method for separating a population of parvoviral virions from a population of baculoviral virions, wherein the method comprises the step of filtrating a sample comprising the populations of parvoviral and baculoviral virions over a filter through which only the parvoviral virions can pass. It is preferred that the filter has a nominal pore size of 30-70 nm, more preferably 30-40, again more preferably 32-38 nm, and most preferably of (about) 35 nm. In a preferred embodiment, the parvovirus is an adeno-associated virus, more preferably the baculovirus is *Autographa californica* multicapsid nucleopolyhedrovirus (AcmNPV).

In a preferred embodiment, the filter to be used in the filtration of the sample is a virus filter or an ultrafilter. It is preferred that the filter is a surface and/or a depth filter. The filter for use in a method of the invention preferably comprises a material selected from the group consisting of: cuprammonium-regenerated cellulose, polyvinylidenefluoride, polysulfone, such as for example polyethersulfone, e.g. modified or unmodified polyethersulfone, polytetrafluoroethylene, polypropylene, modified or unmodified polyethersulfone, cellulose acetate, cellulose nitrate, polyamide or regenerated cellulose. In a particularly preferred embodiment, the filter for use in a method of the invention comprises cuprammonium-regenerated cellulose, preferably cuprammonium-regenerated cellulose hollow fibres, more preferably wherein the filter is a Planova™ 35 membrane (Asahi KASEI; Worldwide web URL planovafilters.com). In another preferred embodiment, the filter for use in a method of the invention is an Ultipor™ VF Grade DV50 Virus Removal Filter (Pall Corp.; Worldwide web URL pall.com).

In an embodiment of a method according to the present invention, the sample is subjected to filtration using two or more filters.

In a method according to the invention, the sample can prior to the step of filtration be prepurified using a method selected from the group consisting of a density gradient, a prefiltration, a chromatography step, preferably affinity chromatography and/or ion-exchange chromatography, and combinations of these methods. Prefiltration is preferably effected by means of a filter with a pore size of 70-200 nm. Preferably, the pH of the sample to be subjected to a method of the invention is 6 to 10, preferably 7 to 9, more preferably 7.5 to 8.5, most preferably about 8. In an embodiment of the invention, 1 to 200 ml of sample is filtered per 1 cm$^2$ of virus filter surface, preferably 80 to 120 ml per 1 cm$^2$.

A method of the invention preferably results in elution of at least 85% of the parvovirus and reduction of the baculovirus with at least 5 logs, i.e., $10*10^5$.

Definitions

The term "virus" or "viruses" as used herein encompasses not only naturally occurring viruses or viruses which have been altered by genetic manipulation, i.e., so-called recombinant viruses, but also virus particles, i.e., both infectious and non-infectious viruses, virus-like particles ("VLP"), such as papillomavirus-like particles in accordance with WO 96/11272, and capsids which contain nucleic acids, but can also be empty, and parts thereof, in particular, one or more, preferably several subunits or capsomers, especially when several capsomers are associated or combined such that they constitute at least approx. 50%, preferably at least 80%, especially approx. 90%, of the capsid. The viruses that are removed from the mixture have, in particular, an essentially non-spherical rod-like shaped structure whereas the viruses that are the pharmaceutical product essentially have a spherical, preferably an icosahedral, shape. It is further understood that the term "virus" may refer to a population of virions of that virus, preferably a homogeneous population of the virus. Thus, the term "parvovirus" may refer to a population of parvoviral virions, preferably a homogeneous population of parvoviral virions.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus Dependovirus. As may be deduced from the name of their genus, members of the Dependovirus are unique in that they usually require coinfection with a helper virus such as adenovirus or herpes virus for productive infection in cell culture.

The genus Dependovirus includes adeno-associated virus (AAV), which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Today, it is possible to differentiate between the serologically distinguishable types of at least AAV-1, AAV-2, AAV-3, AAV-4, AAV-5, AAV-6, AAV-7, AAV-8 and AAV-9. AAV vectors constitute a single-stranded of DNA with an outer icosahedral coat of structural protein having a diameter of 18 to 26 nm, typically about 25 nm. Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses. It is also understood that the invention extends to AAV chimeric viruses, comprising chimeric capsid proteins and/or AAV hybrid viruses (or pseudotyped viruses) that also have a similar size as found for the wild type parvoviruses (18-26 nm diameter). A description and some examples are given in WO0028004. Examples of AAV chimeric and/or hybrid viruses are for example AAV2/1, AAV2/3, AAV2/4, AAV2/5, AAV2/5.2, AAV2/6, AAV2/7, AAV2/8 and AAV2/9.

The AAV genome consists of rep genes encoding proteins required for replication of the virus and cap genes encoding the viral structural proteins. One or more of the rep genes which are required for replication (e.g. rep 40, rep 52, rep 68 and/or rep 78) or the cap genes which are required for the capsid structure (e.g. VP-1, VP-2 and/or VP-3) can, for example, be replaced in the virus with a transgene when preparing adeno-associated vectors. The ITR regions which are still present at the 5' and 3' ends are needed, as cis-active elements, for packaging the transgene into infectious, recombinant AAV particles and for the replication of the DNA of the recombinant AAV genome (Kotin, R. M. (1994) Hum Gene Ther. 5(7):793-801). A "recombinant parvoviral or AAV vector" (or "rAAV vector") herein refers to a vector comprising one or more polynucleotide sequences of interest, genes of interest or "transgenes" that are flanked by parvoviral or AAV inverted terminal repeat sequences (ITRs). Such rAAV vectors can be replicated and packaged into infectious viral particles when present in an insect host cell that is expressing AAV rep and cap gene products (i.e., AAV Rep and Cap proteins). When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions.

An "insect cell" as used herein refers to an insect cell which allows for replication of a recombinant parvoviral (rAAV) vector and which can be maintained in culture. For example, the cell line used can be from Spodoptera frugiperda, drosophila cell lines, or mosquito cell lines, e.g., Aedes albopictus derived cell lines. Preferred insect cells or cell lines are cells from the insect species which are susceptible to baculovirus infection, including e.g. Se301, SeIZD2109, SeUCR1, Sf9, Sf900+, Sf21, BTI-TN-5B1-4, MG-1, Tn368, HzAm1, Ha2302, Hz2E5, High Five (Invitrogen, CA, USA) and expresSF+® (U.S. Pat. No. 6,103,526; Protein Sciences Corp., CT, USA). Growing conditions for insect cells in culture, and production of heterologous products in insect cells in culture are well-known in the art and described e.g. in the following references on molecular engineering of insects cells. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W. H. Freeman and Richardson, C. D., 1995, Baculovirus Expression Protocols, Methods in Molecular Biology, volume 39; U.S. Pat. No. 4,745,051; US2003148506; and WO 03/074714.

Detailed Description of the Invention

Recombinant rAAV can be produced in insect cells using a baculovirus-based expression system, in which the insect cell is infected with three recombinant baculoviruses harbouring the AAV vector and rep and cap functions. When the infected insect cells are cultured, the AAV non-structural protein genes and the AAV structural protein genes are expressed, the transgene DNA is replicated and the recombinant AAV particles (rAAV particles) are packaged and assembled. The rAAV particles contain the gene product(s) of interest (the transgene(s)), which is/are flanked at both ends by the ITR regions, in the form of single-stranded DNA. At the same time, the recombinant baculovirus replicates in these cells, something which generally ends in the lysis and death of the infected cells after a few days. The resulting viruses (baculovirus and rAAV particles) are either in part released into the cell culture supernatant or else remain in the lysed cells. For this reason, the cells are generally disrupted using cell disruption methods which are known to those skilled in the art, such as alternately freezing and thawing or by means of enzymatic hydrolysis, for example with trypsin, in order to achieve essentially complete release of the viruses or by detergent lysis.

A significant disadvantage associated with preparing viral vectors using a virus-based expression system, such as a baculovirus-based expression system or using a helper virus system, is the formation of a mixed population of product virus particles and non-product viruses, which population has to be subjected to further purification. For convenience, the word "helper virus" is used herein to indicate either 'true' helper viruses used in the production of AAV, such as for example adenovirus or herpes virus, or baculovirus, although it is not yet clear if the baculovirus indeed provides helper functions or just delivers the AAV genes in the insect cells. Contaminate baculovirus should be avoided when using viral vectors in gene therapy because of potential pathogenicity or immunogenicity of baculovirus.

Therefore, the present invention provides for a separation/purification method that is suitable, for example to obtain a regulatory approved parvoviral product, that is technically and economically feasible to be employed on industrial scale and that is capable of demonstrating reduction, preferably depletion, of a rod-like shaped virus in a virus sample comprising rod-like shaped virus particles and essentially spherical virus particles, in particular where the rod-shaped virus particles have a similar diameter as the parvoviral particles (i.e., the rod-shaped virus particles are similar in two dimensions, but not in the third dimension, which must be larger), so that potential pathogenicity and/or immunogenicity of the helper virus is reduced. It is appreciated by persons skilled in the art that it is challenging and not likely that a mixture of non-product virus and product virus of which both viruses have a similar size in two dimensions can be separated by filtration techniques, preferably by high levels.

Thus, in a first aspect, the present invention relates to a method for separation of two populations of virions in a sample, preferably wherein one population of virions comprises virions that are of an essentially spherical shape and the other population of virions comprises virions that are of a rod-like shape, the method comprising the step of filtration of a sample comprising both populations of virions over a filter through which only the virions of an essentially spherical shape can pass. Preferably, the virus which has a rod-like shape has an aspect ratio of at least 4:1. It is also preferred that the diameter of the rod-like shape virus and the diameter of the essentially spherical shape do not differ more than 12 nm. It is preferred that the essentially spherical virus is a parvovirus and that the virus of a rod-like shape is a baculovirus. In particular, the invention relates to a method for separating a population of parvoviral virions from a population of baculoviral virions, wherein the method comprises the step of filtrating a sample comprising the populations of parvoviral and baculoviral virions over a filter through which only the parvoviral virions can pass.

The term "separating" as used herein does not implicate that both particles to be separated are recovered from the sample. The term "separating" as used herein indicates partial or complete removal of rod-like shaped virus particles from the sample, and thus reduce contamination of rod-like shaped virus in the sample of essentially spherical virus particles. Thus, separation can be understood to mean purification of the essentially spherical virus particles in the sample. In the case of baculovirus and parvovirus, it can be said that the term "separating" as used herein indicates partial or complete removal of the baculovirus from the sample, and thus reduce contamination of the baculovirus in the sample comprising parvovirus. In this case, separation means purification of the parvovirus in the sample.

Filtration is a physical operation which is used for the separation of for example solids from solids of different size or from fluids, by interposing a medium though which only solids having a size below a given size limit or only the fluid can pass. Oversize solids in the sample are retained in the feed. The fluid, including solids that have passed through the filter may be referred to as the filtrate or permeate.

The process of "virus removal" applied for the present invention is conducted by "filtration", also known as "virus filtration". "Virus filtration" is understood to separate a pharmaceutical product from a viral contaminant by means of a filter, such as a virus filter or an ultrafilter. It is understood that the pharmaceutical product itself may also be a virus, such as a viral (gene therapy) vector.

Virus filtration is a filtration technology wherein a membrane is used with a nominal pore size in the nanometer scale. Virus filters and ultrafilters typically comprise membranes with a nominal pore size in the range of 30 nanometer–1 micrometer or a Molecular Weight Cut off (MWCO) in the range of 10,000-750,000 Dalton, preferably in the range of 10,000-500,000 Dalton, more preferably in the range of 10,000-100,000 Dalton. Classification of the type of filter is dependent on membrane structure, material, and vendor. Also the type of use could determine the classification. One can use ultrafilters in a tangential flow filtration (TFF) modus (also known as cross flow filtration; During recirculation the feed fluid comprising the sample is parallel to the filter and only a part of the feed fluid comprising the sample is used for permeate production, the largest part of the feed fluid will leave the module without having crossed the filter) or use them as a dead end filter (all of the sample is passed through the filter). Terminology is very well understood by a person skilled in the art.

Virus filtration typically uses a pressure difference over the membrane: the transmembrane pressure (pressure drop across the membrane) of between 0.02 and 0.8 MPa, preferably between 0.02 and 0.1 MPa. The pressure difference can be effected by the flow rate applied to the sample (i.e., by a pump). When the filter is operated in a TFF modus a transmembrane pressure can also be modulated by subjecting the sample to pressure prior to the membrane by constricting the retentate line or after the membrane (i.e., in the permeate) by using a pump. These operations can be readily determined by a skilled person in the art.

In a preferred embodiment of the invention, the population of virions that have an essentially spherical shape are virions that have icosahedron symmetry and a diameter of approximately 18-25 nm. Thus, in a preferred embodiment of the present invention, the population of virions that have an essentially spherical shape, is a population of parvoviral virions, preferably adeno-associated virus.

The "aspect ratio" of a shape is the ratio of its longer dimension to its shorter dimension. Thus, for symmetrical objects that are described by just 2 measurements, such as the length and diameter of a rod. Alternatively or in combination with any of the other embodiments of the present invention, in a preferred embodiment of the invention the aspect ratio of the virus with a rod-like shape is at least 4:1, preferably at least 5:1, more preferably at least 6:1, at least 7:1, at least 8:1, at least 9:1, at least 10:1, at least 11:1 at least 12:1, or approximately 13:1. In a population of rod-like shaped virions, such as baculovirus, that are separated using a method of the invention, preferably the virions have a diameter of 18-30 nm, more preferably 20-27 nm, more preferably 20-25 nm, more preferably 20-23 nm and a length of 70 nm-300 nm, preferably of 80 nm-280 nm, 90 nm-260 nm, 100 nm-260 nm, 120 nm-260 nm, 140 nm-260 nm, 160 nm-260 nm, 180 nm-260 nm, 200 nm-260 nm, 220 nm-260 nm, 240 nm-260 nm. More preferably, the virions have a diameter of 20-23 nm and a length of 180-280 nm, in particular a diameter of about 20 nm and a length of about 120-260 mm.

A population of rod-like shaped virions of the present invention preferably is a population of virions which belong to the family of the baculoviridae. The name baculoviridae was proposed because of the rod-shape of their virions, which is derived from Latin baculum=cane, walking stick, staff. The best studied baculovirus is the *Autographa californica* mononucleo polyhedrosis virus (AcmNPV) which is of asymmetric shape and has a diameter of approximately 20-120-260 nm (i.e., approximately 20 nm in two dimensions and approximately 120-260 nm in the third dementia, or alternatively and more preferably phrased: has a diameter of approximately 20 nm and a length of approximately 120-260 nm). The viruses that are classified as baculoviridae genus are *Alphabaculoviruses, Betabaculoviruses, Deltabaculoviruses* and *Gammabaculoviruses* and their respective members are Lepidopteran NPVs, Ledidopteran GVs, Hymenopteran NPVs and the Dipteran NPVs. Since several baculoviruses have been determined to have different genome length it is suggested that capsid length may be flexible in response to the genome length which varies between 80 kb and 160 kb. Examples of baculoviruses that could be separated from a population of parvoviral virions as defined elsewhere herein using a method of the present invention are provided in Table 1 (based on Baculovirus Molecular Biology by G. F. Rohrmann; Second Edition; 26 Jan. 2011; Chapter 1: "Introduction to the baculoviruses and their taxonomy").

TABLE 1

Genome size and predicted ORF content* of selected baculoviruses

| Virus type | Name of Virus | Reference | Size (kb) | Orfs (>50 aa) |
|---|---|---|---|---|
| Group I (12 members)** | EppoMNPV | Hyink O. et al.; J Gen Virol. 2002; 83(Pt 4): 957-71. [PubMed] | 119 | 136 |
| | AnpeNPV | Fan Q. et al.; Virology. 2007; 366(2): 304-15. [PubMed] | 126 | 145 |
| | AcMNPV | Ayres M. D. et al.; Virology. 1994; 202: 586-605. [PubMed] | 134 | ~150 |
| Group II (16 members) | AdhoNPV | Nakai M. et al.; Virology. 2003; 316(1): 171-83. [PubMed] | 113 | 125 |
| | SeMNPV | Ijkel W. F. J. et al.; ; J. Gen. Virol. 1999; 80: 3289-3304. [PubMed] | 136 | 139 |
| | AgseNPV | Jakubowska A. K. et al.; J Gen Virol. 2006; 87(Pt 3): 537-51. [PubMed] | 148 | 153 |
| | LdMNPV | Kuzio J. et al.; Virology. 1999; 253: 17-34. [PubMed] | 161 | 163 |
| | LeseNPV | Xiao H., Qi Y.; Virus Genes. 2007; 35(3): 845-56. [PubMed] | 168 | 169 |
| GV (10 members) | AdorGV | Wormleaton S., Kuzio J., Winstanley D.; Virology. 2003; 311(2): 350-65. [PubMed] | 100 | 119 |
| | CrleGV | Lange M., Jehle J. A.; Virology. 2003; 317(2): 220-36. [PubMed] | 111 | 124 |
| | CpGV | Luque T. et al.; J Gen Virol. 2001; 82(Pt 10): 2531-47. [PubMed] | 124 | 143 |
| | XecnGV | Hayakawa T. et al.; Virology. 1999; 262: 277-297. [PubMed] | 179 | 181 |
| Hymenopt. NPV (3 members) | NeleNPV | Lauzon H. A. et al.; J Gen Virol. 2005; 86: 945-61. [PubMed] | 82 | 89 |

TABLE 1-continued

Genome size and predicted ORF content* of selected baculoviruses

| Virus type | Name of Virus | Reference | Size (kb) | Orfs (>50 aa) |
|---|---|---|---|---|
| | NeabNPV | Duffy S. P. et al.; J Virol. 2006; 80(14): 6952-63. [PubMed] | 84 | 93 |
| | NeseNPV | Garcia-Maruniak A. et al.; J Virol. 2004; 78(13): 7036-51. [PubMed] | 86 | 90 |
| Dipteran NPV (1 member) | CuniNPV | Afonso C. L. et al.; J Virol. 2001; 75: 11157-65. [PubMed] | 108 | 109 |

*Selected from over 40 genome sequences (2008);
**The numbers in brackets indicate the total number of genomes in the category; Group 1: One of two major lineages of lepidopteran NPVs; it is distinguished from other baculoviruses by using a different envelope fusion protein, gp64. Several other genes are also unique to this lineage; Group 2: One of two major lineages of lepidopteran NPVs; members are thought to use a fusion protein (F) to initiate infection; GV: Granulosis viruses: A lineage of baculoviruses pathogenic for Lepidoptera, which normally have a single virion per ovoid-shaped occlusion body; NPV: Nuclear polyhedrosis virus: The most widely distributed type of baculovirus. NPVs replicate in the nucleus and usually produce polyhedron-shaped occlusion bodies containing more than one virion.

In a preferred embodiment of the invention, the population of baculoviral virions is a population of *Autographa californica* multicapsid nucleopolyhedrovirus (AcmNPV). In AAV production systems *Autographa californica* multiple nucleopolyhedrosis virus (AcmNPV) is the baculovirus type of choice. AcmNPV is the most studied baculovirus. The virus was originally isolated from the alfalfa looper (a lepidopteran) and contains a 134 kbp genome with 154 open reading frames. The major capsid protein VP39 together with some minor proteins forms a rod-shaped nucleocapsid (21 nm×260 nm) that encloses the DNA with a p6.9 protein. In the baculovirus-mediated AAV production process, seven of the genes currently screened for AAV replication appear to be related to baculovirus replication (lef-1, lef-2, lef-11, dna-pol, lef-3, lef-7, and dbp and three have been described as encoding trans-activation factors (p35, ie-1, ie-2).

In a preferred embodiment of the invention, the diameter of the rod-like shaped virion and the diameter of the essentially spherical shaped virion differ less than 12 nm in size, preferably less than 11, 10, 9, 8, 7, 6, 5 nm, whereby the spherical shaped virion preferably has the larger diameter of the two. Thus, for example, in the preferred embodiment of the invention wherein a population of parvoviral virions is separated from a population of baculoviral virions, preferably adeno-associated virus, the two types of virions are of partly similar size, since diameter of a parvovirus (e.g. AAV) and baculovirus (in two dimensions) differs less than 5 nm.

A filter for use in the present invention is a membrane with a nominal pore size of preferably 1.2 to 3.3 times the diameter of the virus of a rod-like shape (i.e., the diameter of the shorter dimension, not the length of the rod-like shaped virus). The terms "pore size", "removal rate", "effective size", "nominal pore size" or "pore size which permits particles having a particular minimum size to be removed" as used by different filter manufacturers, are equivalent terms for the purpose of the present invention and can be used interchangeably herein.

Preferably, the membrane has a pore size of at least 1.3, 1.4, 1.5 times the diameter of the virus of a rod-like shape but less than 3.2, 3.1, 3.0, 2.9, 2.7, 2.5, 2.3, 2.1, 1.9, 1.8 times the diameter of the virus of a rod-like shape. More preferably, the membrane has a pore size of 1.6 to 1.7 times the diameter of the virus of a rod-like shape. In a preferred embodiment, the filter for use in a method of the present invention has a pore size of 30 to 70 nm, more preferably 30 to 60 nm, more preferably 30 to 50 nm, more preferably 30 to 40 nm, more preferably 32 to 38 nm, more preferably 34 to 36 nm, most preferably 35 nm. An example of a virus filter having a pore size of 35 nm, for instance is the Asahi-Kasai Planova 35N membrane (Worldwide web URL planovafilters.com). In another preferred embodiment, the filter for use in a method of the invention is an Ultipor™ VF Grade DV50 Virus Removal Filter (Pall Corp.; Worldwide web URL pall.com).

In a preferred embodiment, a filter for use in the present invention is a virus filter or an ultrafilter. A virus filter typically is a filter wherein the pores have a size in the nanometer scale. Preferably, a virus filter is a filter wherein the pores have a size in the nanometer scale and wherein the fibres have asymmetric pores in them, which capture particles of certain sizes and let smaller particles through. Examples of virus filters that can be employed in the present invention are the 35N Planova membrane. Examples of ultrafilters are Pellicon 2 or Pellicon 3 (Millipore), Sartocon (Sartorius) and Centracette (Pall).

In a preferred embodiment of the present invention, the filter, e.g. a 35N Planova filter, employs a surface or depth mechanism or a combination of the two for the discrimination of the viruses of differing morphologies. Surface filtration is pore-size based and involves that during filtration the particles with a larger diameter than the pore diameter are retained at the surface on the 'flow-in' side of the filter and a 'cake' is formed. In contrast, in depth filtration, particles are trapped inside the filter medium because of the composition of the individual fibre layer: typically at the flow-in side the layer consists of coarse fibres and at the flow-out side the layer consists of fine fibres. Depth filters are the variety of filters that use a porous filtration medium to retain particles throughout the medium, rather than just on the surface of the medium. These filters are commonly used when the fluid to be filtered contains a high load of particles because, relative to other types of filters, they can retain a large mass of particles before becoming blocked.

It is noted that "filter membrane" is understood to mean the actual filter material that is doing the sieving, in all filters. Advantageously, the filter membranes used are composed of preferentially regenerated cellulose, for example cuprammonium-regenerated cellulose, such as preferably cuprammonium regenerated cellulose hollow fibres, but other suitable materials are polyvinylidenefluoride, polytetrafluoroethylene, polypropylene, modified or unmodified polyethersulfone, cellulose acetate, cellulose nitrate or polyamide. Examples of such membranes having a pore size which permits the removal of particles having a size of approx. 40-400 nm are the Ultipor VF membranes from Pall GmbH, 63303 Dreieich, which have nominal pore sizes of approx 50 nm or 20 nm, the Asahi Chemical's Bemberg microporous membranes from Asahi Chemical Industry Ltd., Tokyo, Japan, which have nominal pore sizes of approx. 15, 19, 35 or 72 nm, or corresponding membranes from other manufacturers i.e., Sartorius AG, 37075 Gottingen or Schleicher and Schuell GmbH, 37582 Dassel. In a preferred embodiment of the invention, the filter comprises cuprammonium-regenerated cellulose, polyvinylidenefluoride, polysulfone, polytetrafluoroethylene, polypropylene, modified or unmodified polyether sulfone, cellulose acetate, cellulose nitrate, polyamide or regenerated cellulose, preferably wherein the filter contains cuprammonium-regenerated cellulose hollow fibres or polyvinylidenefluoride.

A method of the present invention is particularly suitable for purification of a population of parvoviral virions from a population of baculoviral virions. Indeed, a virus filter having a pore size of 35 nm, e.g. the Asahi-Kasai Planova 35N membrane, is particularly advantageous in a method of the invention for separating rAAV particles and baculovirus. These filters especially make it possible not only to achieve an essentially quantitative removal of infectious baculoviruses of at least 5 log 10 from the mixed population but also to achieve a high yield, of approximately >90%, of rAAV particles.

A reduction in titer of a rod-like shaped virus, i.e., the factor by which the titer of the virus to be removed is decreased, is preferably at least 5 logs, e.g. after a mixed population of rAAV virions and $10 \times 10^5$ baculoviral virions had been separated in accordance with a method of the invention, no baculoviral virions were then detected in the filtrate. Preferably, the reduction in titer of a rod-like shaped virus that is achieved by a method of the invention is at least 5.5 logs, at least 6 logs, at least 6.5 logs, at least 7 logs, at least 8 logs, at least 9 logs, most preferably at least 10 logs. The titer can be determined by general methods known in the art, such as for example by a Tissue Culture Infectious Dose 50% (TCID50) assay. For example, the infectious baculovirus titer of a population of baculoviral virions in a sample can be determined using a TCID50 assay. This method is based on the infection of monolayers of Sf9 insect cells with infectious baculovirus in a positive control sample. A serial dilution in culture medium of the positive control sample is used to infect the cells. The cells are incubated at +28° C. for 7 days. Subsequently, the supernatants are transferred to newly prepared plates with monolayers of Sf9 insect cells and incubated at +28° C. for 7 days. As infection proceeds, the infected cells are not able to remain attached to each other and to the plate surface and form loose cells, i.e., show cytopathogenic effect (CPE), which can be observed microscopically. The titer in log 10 TCID50/mL is calculated using the Spearman-Kärber method.

Preferably, at least 60%, 65%, 70%, 75%, 80%, 85%, 87%, 90%, 93%, 95%, 97%, 99% of the population of virions of essentially spherical shape is recovered using a method of the invention. Thus, preferably at least 60%, 65%, 70%, 75%, 80%, 85%, 87%, 90%, 93%, 95%, 97%, 99% of the population of virions of essentially spherical shape is recovered in the eluate (or permeate).

In a preferred embodiment of the invention, the sample is filtered through two or more filters.

A sample comprising the populations of virions to be separated is typically a culture supernatant (e.g. culture medium) from a virus-based expression system, e.g. from an insect cell culture to produce the AAV virions, insect cells from a virus-based expression system to produce AAV virions, or a combination of culture supernatant and insect cells. Preferably, the sample is subjected to freeze-thaw cycles before being used in a method of the present invention. More preferably, the sample is subjected to pre-purification before use in the method of the present invention. This may increase the yield across the filtration of the population of virions of essentially spherical shape (e.g. the parvoviral virions, preferably AAV) and it is also believed to be advantageous for the life span of the filter. Thus, in a preferred embodiment the sample is free of cellular contaminants.

Thus, in a preferred embodiment, the method comprises pre-purification of the sample comprising the populations of virions, for example by means of centrifugation, one or more density gradients, pre-filtration and/or chromatography. Preferably, the sample is pre-purified in case the sample is for example a supernatant of an rAAV culture, for example by pre-filtration to remove larger particles and wherein the baculovirus and the rAAV particles are retained in the filtrate. Advantageously, a pre-filtration, as described in more detail below, is carried out prior to the actual separation of the populations of virions as described earlier herein. In a preferred embodiment, the sample is pre-purified using a method selected from the group consisting of a density gradient, a pre-filtration, a chromatography step, preferably affinity chromatography and/or ion-exchange chromatography, and combinations of these methods. Examples of such purification method include Brument et. al., 2002 Molecular Therapy, Kaluduv et. al., 2002 Human Gene Therapy, Potter et. al., 2002 Methods in Enzymology and Cecchini et. al., 2010 Human gene therapy. Preferably, pre-purification comprises density gradient and one or more pre-filtrations and/or centrifugation steps. Preferably, pre-purification comprises one or more pre-filtrations in combination with one or more chromatography steps.

Particular preference is given to a pre-purification of the sample using one or more membrane filters which allow the populations of virions which are to be separated to pass but which nevertheless retain larger impurities. In general, the pre-purification prevents, or renders more difficult, the blocking of the filter that is used in a method of the invention which brings about the subsequent separation of the populations of rod-like shaped and essentially spherical virions. Blocking of the filter during separation of the populations of virions may occur by constituents of the virus culture in the sample which are not removed, or are not adequately removed, before subjecting the sample to a method of the invention. Centrifugation at low speed may not be sufficient to adequately remove such constituents, therefore further pre-purification of the sample is preferred to minimize blocking of the filter.

Preferably, pre-purification is carried out by pre-filtration. The membrane filter for pre-purifying a sample comprising AAV and baculovirus and that is to be subjected to a method of the invention, preferably has a pore size of 70 to 200 nm, more preferably 80 to 180 nm, 90 to 150 nm, 100 to 130 nm. For example, a membrane filter having a pore size of approximately 100 nm, such as the Ultipor N66 filter (Pall GmbH, 63303 Dreieich), is particularly well suited for pre-purifying a mixed population of rAAV particles and baculoviruses. Thus, in a preferred embodiment, the prefiltration is effected by means of a filter with a pore size of 70 to 200 nm.

Suitable methods and means for pre-purification depend on the filter that is to be used in the method of the invention for separation of the populations of parvoviral and baculoviral virions as earlier described herein, and can be tested by the skilled person. The conditions after prepurification must be so that 1) the filter remains integral, 2) the parvovirus is stable, 3) the salt concentrations are close to physiological and 4) the pressure drop over the filter is not so large that it causes the parvovirus (e.g. AAV) to 'lyse' and thus no longer functional.

In another preferred embodiment, the pH of the sample is 6 to 10, preferably 7 to 9, more preferably 7.5 to 8.5, in particular approximately 8.0. If necessary, the pH of the sample is adjusted with suitable buffers, for example Tris/HCl buffers (tris(hydroxymethyl)amino-methane), to the pH as specified above. The pH of the sample is preferably about 8.0, since that results in a good yield of AAV after filtration.

In a preferred embodiment of the invention, the sample has pH of 6-8.5 (essentially physiological) to ensure that the AAV is stable. A buffer with a pH in this range should preferably also have a conductivity that is suitable for the particular parvovirus. Typically, the required conductivity depends on the serotype of AAV and on the transgene. The skilled person is capable of determining a suitable buffer on a case to case basis. Typically, the background conductivity should be comparable to physiological conductivity i.e., 137 mM NaCl. Examples of suitable buffer solutions are MES, Trizma, Bis-Tris, HEPES, PBS and Bis-Tris Propane.

In a preferred embodiment, at least 0.5 ml of sample is filtered per 1 cm$^2$ of filter surface, preferably 1 to 100 ml per 1 cm$^2$. However, this is highly dependent on the purity and concentration of the viruses in the sample to be separated and in most events since the filtration is applied at the end of the downstream process more than 1 L can be filtered per 1 cm$^2$. Alternatively or in combination with any of the other preferred embodiments, in a preferred embodiment of the invention at least 1-10 ml, preferably 1-5 ml, in particular about 1.5 ml, of the sample is filtered per 1 cm$^2$ of filter surface. In general, this achieves a high yield of rAAV particles, for example, while at the same time achieving the removal of the baculoviruses.

Thus, the present invention provides a method that results in separation/purification of a population of virions of an essentially spherical form and a population of virions with a rod-like shape in a simple and inexpensive manner and which method can be applied on an industrial scale. A method of the invention can be employed under particularly mild conditions and results in a high yield of virions of essentially spherical shape whereas the virions with a rod-like shape are reduced or even eliminated from the filtrate. A further advantage of the present invention is that the virions which have been purified in accordance with the invention can, for example, be employed directly as viral vectors for gene therapy since they are adequately free of other viruses, for example baculoviruses. Although small residual fractions of baculovirus DNA may remain in the filtrate this DNA however is not associated with replication-competent baculoviruses but rather associated with co-packed DNA in the rAAV and this consequently does not represent infectious baculovirus.

In a preferred embodiment, baculovirus constituents, such as for example free baculovirus proteins and subviral particles, are decreased by the method of the invention. This is particularly advantageous, since these constituents are capable of inducing a nonspecific immune response when the viral vectors are used in gene therapy in a patient.

Alternatively or in combination with embodiments described above, it is an embodiment of the invention that the method of the present invention can be applied for separating more than two different populations of virions, such as for example when a baculoviral expression system is used employing more than one different baculoviral vectors and thus resulting in multiple types of baculoviral virions. The method of the present invention as described above can be used to separate the baculovirus populations from the parvoviral virion population. Thus, the present invention also relates to a method for separation of at least two populations of virions in a sample, preferably wherein one or more populations of virions comprises virions that are of an essentially spherical shape and one or more other populations of virions comprises virions that are of a rod-like shape, the method comprising the step of filtration of a sample comprising the populations of virions over a filter through which only the virions of an essentially spherical shape can pass.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

The figure show the recovery as % input of genome copies and total particles of the filtrate including correction made for sample volumes, the membrane post use wash and the pool of the aforementioned aliquots.

Figure 2:
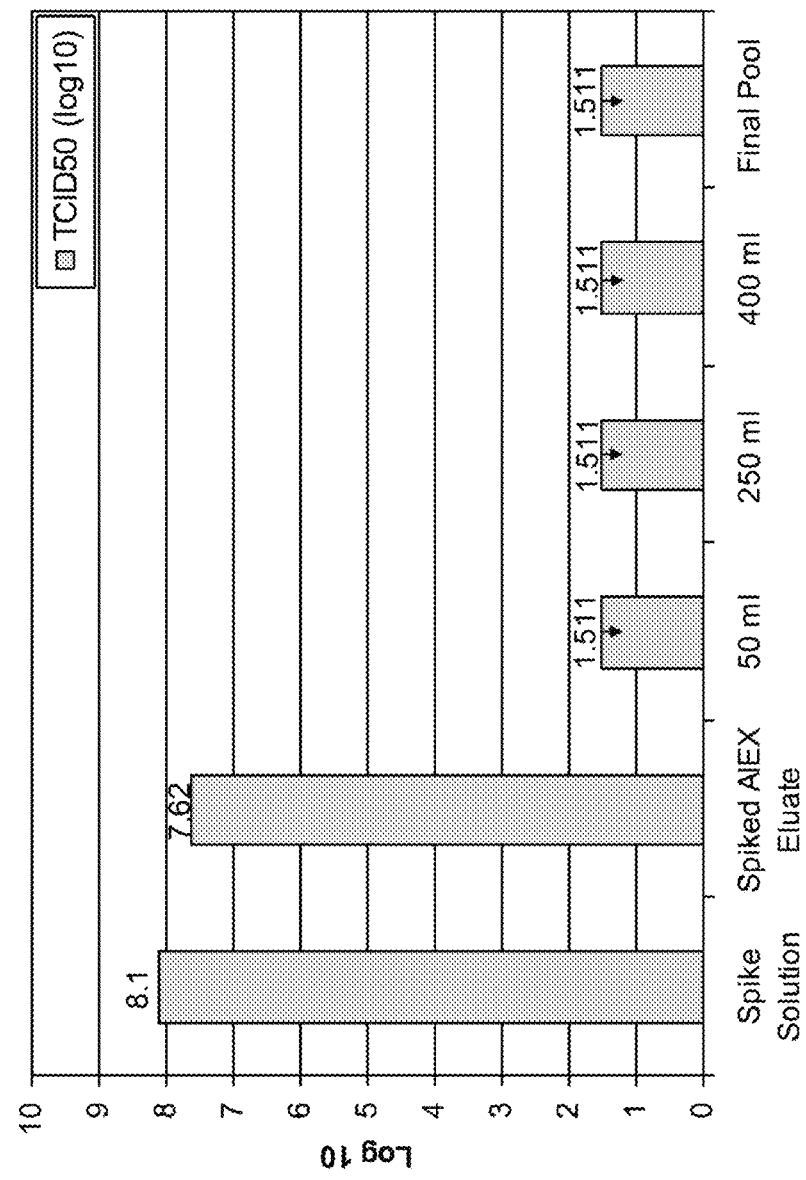

FIG. 2: Baculovirus reduction during virus filtration

The figure shows the baculovirus titre as measured by $TCID_{50}$ of the baculovirus spike material, the virus filter feed (spiked AIEX eluate), nanofiltrate as function of filtration volume (xmL) and the final pool of the virus filter filtrate and virus filter wash. The filtrates and the final pools are the maximum possible titres as the assay returned no well positive for baculovirus.

EXAMPLES

Example 1

Adeno-associated viral vector (AAV) was produced following infection of insect cells with three recombinant baculoviruses as previously described by Urabe et al., 2002 (Hum. Gene Ther 13(16):1935-1943).

Three days after infection the cell culture was detergent lysed and subsequently nuclease treated by the addition of 9 U/mL Benzonase (Merck) and incubation at manufacturer's recommendations.

The crude lysed bulk was subsequently clarified by filtration with a Pall Profile® Star and Pall Supor® filters (Pall Corporation) in series. A viral reduction incubation in the presence of detergent was performed at least 28° C. This material was purified via affinity chromatography using AVB Sepharose HP, GE Healthcare. Briefly, the filtered cell lysate was applied to a 20 cm diameter column (BPG 200/500, GE Healthcare with approximately 6 cm bed height at a linear velocity of 150 cm/hr. The column was washed with phosphate buffered saline until the UV absorbance curve returned to baseline and stabilized. The adsorbed rAAV particles were eluted in acidic media (50 mM sodium citrate adjusted with HCl to pH 3.0) and the column eluate was adjusted immediately with 1/10 volume of 1M Tris-Cl (pH 8.0).

To this neutralized eluate a 10% v/v Baculovirus spike, manufactured as previously described by Urabe et al. (2002; supra) after clarification via centrifugation at 1900 g for 15 minutes and filtration across a 0.2 μm bottle top filter (Corning), was added to provide a mixed population of Baculovirus and AAV for feed to the virus filter.

Prior to use, a Planova 35N Filter was prepared according to the manufacture recommendations. Briefly, the storage solution was removed and all air purged by the addition of 40 ml of 60 mM Tris/HCL pH 8.0 and the flushing procedure was performed according to the manufacture recommendations.

The feed flow rate to the virus filter was set at 5 ml/min as recommended by the manufacture (see Table 2) using a peristaltic pump. During virus filtration, the feed pressure and permeate flow were monitored (see Table 2).

TABLE 2

Virus filtration performance

| Process time (min) | Pump speed (rpm) | Feed pressure (mBar) | volume processed (mL) | Permeate flow (mL/min) |
|---|---|---|---|---|
| 0 | 3 | 160 | 0 | 5 |
| 10 | 3 | 160 | 50 | 5 |
| 20 | 3 | 160 | 100 | 5 |
| 30 | 3 | 160 | 150 | 5 |
| 40 | 3 | 160 | 200 | 5 |
| 50 | 3 | 160 | 250 | 5 |
| 60 | 3 | 160 | 300 | 5 |
| 70 | 3 | 160 | 350 | 5 |
| 80 | 3 | 160 | 400 | 5 |

Samples were collected after 50, 250 and 400 ml filtrate were taken for Baculovirus titration via $TCID_{50}$ assay for infectious baculovirus using Sf9 cell lines. Results are given in TCID50: 50% tissue culture infective dose, which indicates the amount of virus that is required to produce a cytopathic effect in 50% of inoculated tissue culture sf9 cells.

Samples, circa 1 ml, were taken of the filtrate; these were analyzed on Genome Copies (henceforth referred to as GC) of the gene of interest in AAV, and Total Particle (henceforth referred to as TP) of AAV, to monitor their associated recoveries. GC and TP analysis was performed as described below.

To determine the genome copy concentration of samples, ten-fold serial dilutions of test samples and a qualified working standard are prepared, extraneous DNA is removed by DNase digestion and the encapsidated DNA freed by proteinase K digestion. The released viral DNA is then purified using MagneSil Blue®. Subsequently, the DNA is amplified with quantitative-PCR (Q-PCR) using primers specific for the vector genome sequence. DNA amplification is monitored in real-time by inclusion of the fluorescent DNA binding dye SYBR green. The amount of DNA present in a sample can be calculated by comparing the Ct values found for the test sample with that found for the working standard. A parallel-line-assay design is used to test the serial dilutions of the test sample against the qualified working standard, which provides a ratio. This ratio is transformed to the genome copy concentration (gc/mL) using the working standard genome content.

The total number of AAV particles (both the full particles containing a correct genome (vector particles) as well as empty particles) is determined using gel filtration chromatography. Gel filtration HPLC is performed using a BioBasic SEC-1000 (Thermo Electron Corporation) at a flow rate of 1 mL/min with an aqueous phase of D-PBS at 25° C. Elution is monitored with UV absorbance at 214 nm. The peak areas of the test samples are quantified using a calibration curve of a qualified working standard with a known amount of AAV particles per mL.

Figure 1:
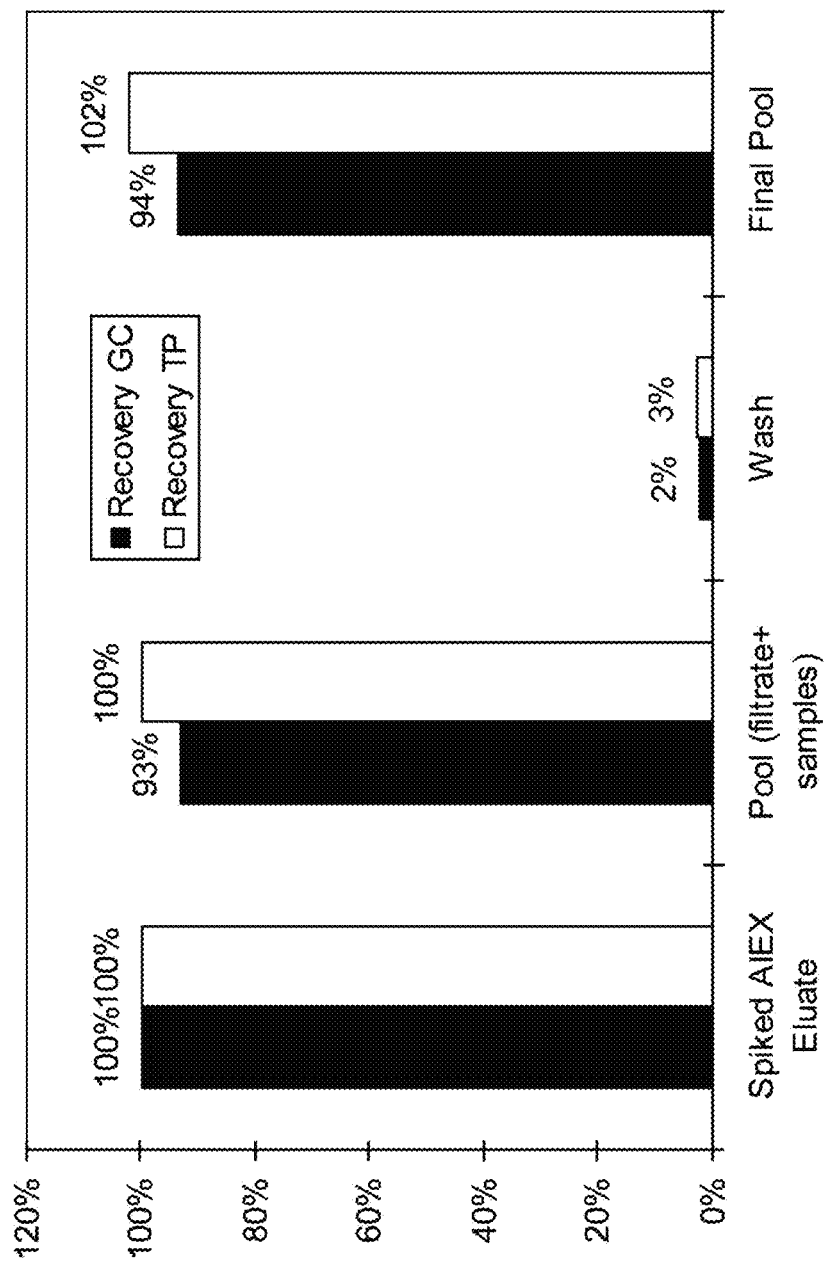
FIG. 1: Recovery of GC and TP during virus filtration.

The Planova 35N filter was washed using 10 ml of 60 mM Tris/HCl pH 8.0 as per manufactures instructions. The wash was pooled with the filtrate and sampled for baculovirus infectious titre via $TCID_{50}$ assay. The wash was sampled for later GC and TP titre determination before being pooled with the filtrate material. The pool of the filtrate and wash were mixed by hand to ensure homogeneity and sampled for later GC and TP titre determination. From the TP and GC titres recovery were calculated and are displayed in FIG. 1

The infectious baculovirus titer of samples is determined using a Tissue Culture Infectious Dose 50% (TCID50) assay. This method is based on the infection of monolayers of SD insect cells with infectious baculovirus in a test sample. A 3-fold serial dilution in culture medium of the test sample is used to infect the cells in octoplicate. The plate is incubated at +28° C. for 7 days. Subsequently, the supernatants are transferred to newly prepared plates and incubated at +28° C. for 7 days. As infection proceeds, the infected cells are not able to remain attached to each other and to the plate surface and form loose cells, i.e., show cytopathogenic effect (CPE), which can be observed microscopically. The titer in log 10 TCID50/mL is calculated using the Spearman-Karber method.

Results

The results for Baculovirus titration are in FIG. 2

The spike solution has an infectious baculovirus titre of 8.1 $\log_{10}$ $TCID_{50}$/mL. The spike solution is added at 10% in the spiked AIEX Eluate, of 7.62 $\log_{10}$ $TCID_{50}$/mL. The $TCID_{50}$ value of the Nanofiltrate declines with at least 6 logs, to below 1.511 $\log_{10}$ $TCID_{50}$/mL, the level of quantification of this particular assay. Therefore nanofiltration gives at least a reduction in Baculovirus of 6 logs, therefore Nanofiltration is a feasible unit operation for the discrimination of two virus with comparable sizes in two dimensions.

The invention claimed is:

1. A method for removing baculoviral virions from a sample comprising parvoviral virions and baculoviral virions, which method comprises filtering the sample through a filter that has a pore size of 30-40 nm, thereby removing the baculoviral virions from the sample.

2. The method according to claim 1, wherein the parvoviral virions are adeno-associated virus virions.

3. The method according to claim 1, wherein the baculoviral virions being removed are virions of *Autographa californica* multicapsid nucleopolyhedrovirus.

4. The method according to claim 1, wherein the filter is a virus filter or an ultrafilter.

5. The method according to claim 1, wherein the filter is a surface and/or a depth filter.

6. The method according to claim 1, wherein the filter comprises a material selected from the group consisting of: regenerated cellulose, polyvinylidene fluoride, polysulfone, polytetrafluoroethylene, polypropylene, modified polyethersulfone, unmodified polyethersulfone, cellulose acetate, cellulose nitrate, and polyamide.

7. The method according to claim 1, wherein the filter has a pore size of 32-38 nm.

8. The method according to claim 6, wherein the regenerated cellulose filter is a cuprammonium-regenerated cellulose filter.

9. The method according to claim 1, wherein the sample is filtered through two or more filters.

10. The method according to claim 1, wherein prior to the filtering step, the sample is prefiltered through a filter with a pore size of 70-200 nm.

11. The method according to claim 1, wherein the pH of the sample is 6 to 10.

12. The method according to claim 1, wherein 1 ml to 200 ml of the sample is filtered per $cm^2$ of filter surface area.

13. The method according to claim 1, wherein the filtering results in:
   (a) recovery of at least 85% of the parvoviral virions; and
   (b) at least a $10^5$-fold reduction in baculoviral virion titer.

14. The method according to claim 8 wherein the cuprammonium-regenerated cellulose filter is a hollow fiber filter.

15. The method according to claim 6 wherein the filter is a hollow fiber membrane comprising cuprammonium regenerated cellulose, or a membrane comprising hydrophilic modified polyvinylidenefluoride.

16. The method according to claim 11 wherein the sample pH is 7 to 9.

17. The method according to claim 11 wherein the sample pH is 7.5 to 8.5.

18. The method according to claim 11 wherein the sample pH is about 8.0.

19. The method according to claim 12 wherein 80 to 120 ml of the sample are filtered per $cm^2$ of the filter surface area.

* * * * *